(12) United States Patent
Yan et al.

(10) Patent No.: US 10,761,015 B1
(45) Date of Patent: Sep. 1, 2020

(54) HANDHELD HEMOGLOBIN DETECTING DEVICE

(71) Applicant: REDEYE INC., Hsinchu (TW)

(72) Inventors: Shuo-Ting Yan, Hsinchu (TW); Tsung-Jui Lin, Hsinchu (TW); L-Hua Wang, Hsinchu (TW)

(73) Assignee: Taiwan RedEye Biomedical Inc., Hsinchu (TW)

( * ) Notice: Subject to any disclaimer, the term of this patent is extended or adjusted under 35 U.S.C. 154(b) by 0 days.

(21) Appl. No.: 16/574,263

(22) Filed: Sep. 18, 2019

(51) Int. Cl.
*G01N 21/27* (2006.01)
*B01L 3/00* (2006.01)
(Continued)

(52) U.S. Cl.
CPC ......... *G01N 21/27* (2013.01); *A61B 10/0038* (2013.01); *B01L 3/508* (2013.01);
(Continued)

(58) Field of Classification Search
CPC .......... A61B 10/08; G01N 2201/0221; G01N 2201/0638; G01N 2201/0694; G01N 33/48; G01N 33/483; G01N 33/487; G01N 33/49; G01N 33/72; G01N 33/721; G01N 33/723; G01N 33/726; G01N 1/02; G01N 1/10; G01N 2001/1031; G01N 2001/1043; G01N 21/01; G01N 21/17; G01N 21/25; G01N 21/251; G01N 21/255; G01N 21/27; G01N 21/31; G01N 21/3103; G01N 21/314; G01N 21/3151; G01N 21/3577; G01N 21/3581; G01N 21/359; G01N 21/47; G01N 21/4738; G01N 21/474; G01N 21/49; G01N 21/51; G01N 21/55; G01N 21/59; G01N 21/62; G01N 21/63; G01N 21/64; G01N 2021/0106; G01N 2021/0112; G01N 2021/0118; G01N 2021/015; G01N 2021/0156; G01N 2021/1734; G01N 2021/1736; G01N 2021/1738; G01N 2021/174; G01N 2021/1742;
(Continued)

(56) References Cited

U.S. PATENT DOCUMENTS

3,327,584 A * 6/1967 Kissinger ............. G01B 11/026
356/614
3,910,701 A * 10/1975 Henderson ........... G01N 21/255
356/39
(Continued)

*Primary Examiner* — Gordon J Stock, Jr.
(74) *Attorney, Agent, or Firm* — Rosenberg, Klein & Lee (57) ABSTRACT

A handheld hemoglobin detecting device has a housing assembly including a holding base, a tubular housing and a liquid holder, a control module disposed on the housing assembly, and a lighting assembly mounted in the tubular housing and including a light emitting module, a light concentrator, and a light guide. At least one light beam emitted from the light emitting module passes through and is concentrated by the light concentrator to shine on the liquid holder, is reflected by a light reflector that is disposed in the liquid holder, enters the light guide, and is transmitted to a light sensor. The handheld hemoglobin detecting device has a simplified structure and is easy to assemble, and thus is light and has low manufacturing cost. Moreover, a lower accuracy in assembling the lighting assembly can be tolerated.

20 Claims, 9 Drawing Sheets

(51) Int. Cl.
*G01N 21/25* (2006.01)
*A61B 10/00* (2006.01)
*G01N 33/487* (2006.01)
*G01N 33/49* (2006.01)
*G01N 21/31* (2006.01)
*G01N 33/72* (2006.01)

(52) U.S. Cl.
CPC ....... *G01N 21/255* (2013.01); *G01N 21/3103* (2013.01); *G01N 33/487* (2013.01); *G01N 33/49* (2013.01); *G01N 33/721* (2013.01); *B01L 2300/041* (2013.01); *B01L 2300/06* (2013.01); *B01L 2300/0627* (2013.01); *B01L 2300/0832* (2013.01); *B01L 2300/0848* (2013.01); *G01N 2201/0221* (2013.01); *G01N 2201/0638* (2013.01); *G01N 2201/0694* (2013.01)

(58) Field of Classification Search
CPC ... G01N 2021/1748; G01N 2021/1753; G01N 2021/3144; G01N 2021/3148; G01N 2021/317; G01N 2021/3181; G01N 2021/4742; G01N 2021/4745; G01N 2021/4747; G01N 2021/475; G01N 2021/4752; G01N 2021/4754; G01N 2021/4757; G01N 2021/4759; G01N 2021/4764; G01N 2021/4769; G01N 2021/4776; G01N 2021/588; B01L 2300/041; B01L 2300/06; B01L 2300/0627; B01L 2300/0809; B01L 2300/0832; B01L 2300/0848; B01L 3/508
USPC .................................................... 356/39–40
See application file for complete search history.

(56) References Cited

U.S. PATENT DOCUMENTS

| | | | | |
|---|---|---|---|---|
| 4,974,094 A * | 11/1990 | Morito | ............... | G02B 21/084 348/359 |
| 5,051,551 A * | 9/1991 | Doyle | ............... | G01N 21/552 250/341.2 |
| 5,701,181 A * | 12/1997 | Boiarski | ............. | G01N 21/474 250/227.2 |
| 5,969,846 A * | 10/1999 | Kishi | ................ | G02B 21/0064 359/227 |
| 6,137,108 A * | 10/2000 | DeThomas | ............ | G01J 3/42 250/339.07 |
| 6,844,931 B2 * | 1/2005 | Ehbets | .................... | G01J 3/02 356/328 |
| 7,359,060 B2 * | 4/2008 | Ebersole | ............... | G01N 21/31 356/451 |
| 7,459,713 B2 * | 12/2008 | Coates | .................... | G01J 3/02 250/239 |
| 7,582,874 B2 * | 9/2009 | Reminiac | ........... | G01N 15/0227 250/341.2 |
| 8,169,470 B2 * | 5/2012 | Ishihara | ............. | A61B 1/00009 348/68 |
| 8,383,414 B2 * | 2/2013 | Reynolds | ............. | G01N 21/251 436/169 |
| 8,957,387 B2 * | 2/2015 | Sexton | ................... | G01N 21/59 250/373 |
| 9,122,016 B2 * | 9/2015 | Takaoka | ............. | A61B 1/00096 |
| 10,309,832 B2 * | 6/2019 | Marquardt | ............... | G01J 3/44 |
| 10,393,652 B2 * | 8/2019 | Karamavu | ........... | G01N 21/474 |
| 10,422,743 B2 * | 9/2019 | Hruska | ................ | G01J 3/0272 |
| 2005/0261605 A1 * | 11/2005 | Shemer | ................ | G01N 21/31 600/573 |
| 2010/0069720 A1 * | 3/2010 | Fulghum | ............... | A61B 1/043 600/175 |
| 2013/0258341 A1 * | 10/2013 | Day | ....................... | G01J 3/108 356/402 |
| 2019/0323949 A1 * | 10/2019 | Carvalho Sousa | .. | G01N 21/255 |

* cited by examiner

HANDHELD HEMOGLOBIN DETECTING DEVICE

BACKGROUND OF THE INVENTION

1. Field of the Invention

The present invention relates to a detecting device, especially to a handheld hemoglobin detecting device.

2. Description of the Prior Art(s)

Hemoglobin exists in the blood of humans and most animals. When tissue inflammation, cancer tissue growth, or ulcers occur in internal organs, blood might leak from the damaged tissue, causing hemoglobin to appear in secretion such as stool, urine, saliva, or snivel. Therefore, detecting the hemoglobin in such secretion can be a crucial index for some specific lesions or diseases. For instance, stool occult blood test is an index for colorectal cancer, urine occult blood test is an index for bladder cancer, and sputum occult blood test is an index for bronchitis or lung cancer.

Among all cancers, colorectal cancer is one of the most commonly diagnosed cancers around the world. In the USA, 8% of the total cancer cases is colorectal cancer, which is ranked the $4^{th}$ among all cancers with a mortality rate ranked the second. China has 18.6% of the global colorectal cancer cases, with 20.1% of the mortalities in the world.

As stated above, one of the most commonly used indexes for colorectal cancer is the occult blood test. In other words, if blood or hemoglobin appears in the stool, it is likely that colorectal cancer or early stage symptom of such is appearing.

Nowadays, the most common solution for stool occult blood test is immunochemical fecal occult blood test (i-FOBT). In the procedure of i-FOBT, the subject is required to collect a sample of the fecal secretion, and send the sample back to the hospital by delivery or in person, so that the medical technologist can perform the occult blood test on the sample. However, such process needs long waiting time and leads to inconvenience, so normally the general public may only go through related physical examinations once a year or two. The inspection cycle is too long to discover the symptom as soon as it shows.

Moreover, blood tissue is not uniformly distributed in the stool, and the sample is only a small portion of the stool that may not include the part that contains blood, leading to a pseudo-negative result, which means the result of the occult blood test is negative, but a tumor or a polyp is already growing inside the intestine and causes bleeding. Furthermore, a tumor or a polyp may be bleeding intermittently instead of constantly. If the lesion did not bleed before or on the day the fecal sample is taken, the result of the occult blood test might also be pseudo-negative and leads to misdiagnosis.

In one of the related arts of remotely detecting stool or urine occult blood, a fluorescent agent or oxidant must be added into the toilet bowl before irradiating the solution in the toilet bowl with excitation light, and then detecting the photoluminescence from the solution to determine whether the secretion contains hemoglobin or blood. The operator must prepare the chemicals, leading to inconvenience.

In some other related art of remotely detecting stool or urine occult blood which also utilizes photoluminescence detection method, analyte such as stool or urine must be added into a reaction solution. The reaction solution includes multiple strong reducing agents that may cause burn when in contact with the skin.

In another related art, the operator of an occult blood test must collect the sample of the stool, and put it in the dilution liquid. After the testing process, a container for containing the stool must be cleaned with extra cleaning processes.

To sum up, among the related arts of secretion occult blood test, some require collected sample of stool or urine, while some require the use of additional chemicals for reaction such as fluorescent agent or reducing agent. Those procedures are complex and inconvenient, or even lead to potential danger, which may not be done frequently and may not be suitable for users to conduct at home.

To overcome the shortcomings, the present invention provides a handheld hemoglobin detecting device to mitigate or obviate the aforementioned problems.

SUMMARY OF THE INVENTION

The main objective of the present invention is to provide a handheld hemoglobin detecting device that comprises a housing assembly, a control module, and a lighting assembly.

The housing assembly includes a holding base, a tubular housing, and a liquid holder. The tubular housing extends from the holding base and has a through hole formed through a distal end surface of the tubular housing. The liquid holder is spaced from the distal end surface of the tubular housing, is attached to the tubular housing via at least one connecting bar, and has a light reflector disposed in the liquid holder.

The control module is disposed on the housing assembly and includes a micro-controller, a switch electrically connected to the micro-controller and alternatively switching the micro-controller on or off, a light sensor electrically connected to the micro-controller, and a display interface electrically connected to the micro-controller.

The lighting assembly is mounted in the tubular housing and includes a light emitting module, a light concentrator, and a light guide. The light emitting module is electrically connected to the micro-controller and has at least one light source. The light concentrator is disposed between the light emitting module and the liquid holder. At least one light beam emitted from the at least one light source passes through and is concentrated by the light concentrator to shine on the liquid holder. The light guide is mounted through the light emitting module and the light concentrator.

The handheld hemoglobin detecting device has a simplified structure and is easy to assemble. Thus, the handheld hemoglobin detecting device is light and has low manufacturing cost. Moreover, a lower accuracy in assembling the lighting assembly can be tolerated.

Other objectives, advantages and novel features of the invention will become more apparent from the following detailed description when taken in conjunction with the accompanying drawings.

DETAILED DESCRIPTION OF THE PREFERRED EMBODIMENTS

With reference to FIGS. 1, 2, 4, and 7, a handheld hemoglobin detecting device in accordance with the present invention comprises a housing assembly 10, a control module 20, and a lighting assembly 30, 30'.

Figure 2:
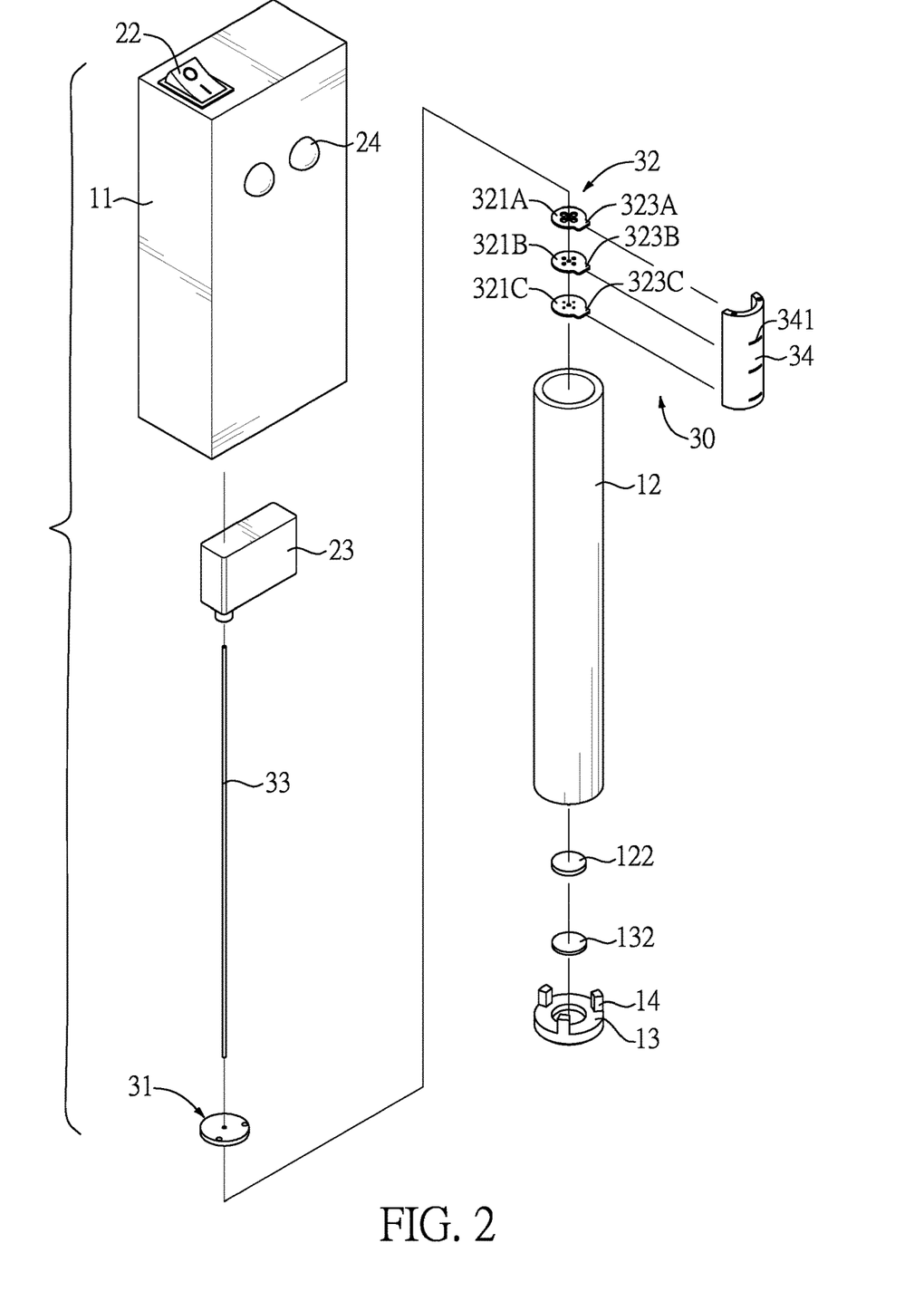
FIG. 2 is an exploded perspective view of the handheld hemoglobin detecting device in FIG. 1.
Figure 4:
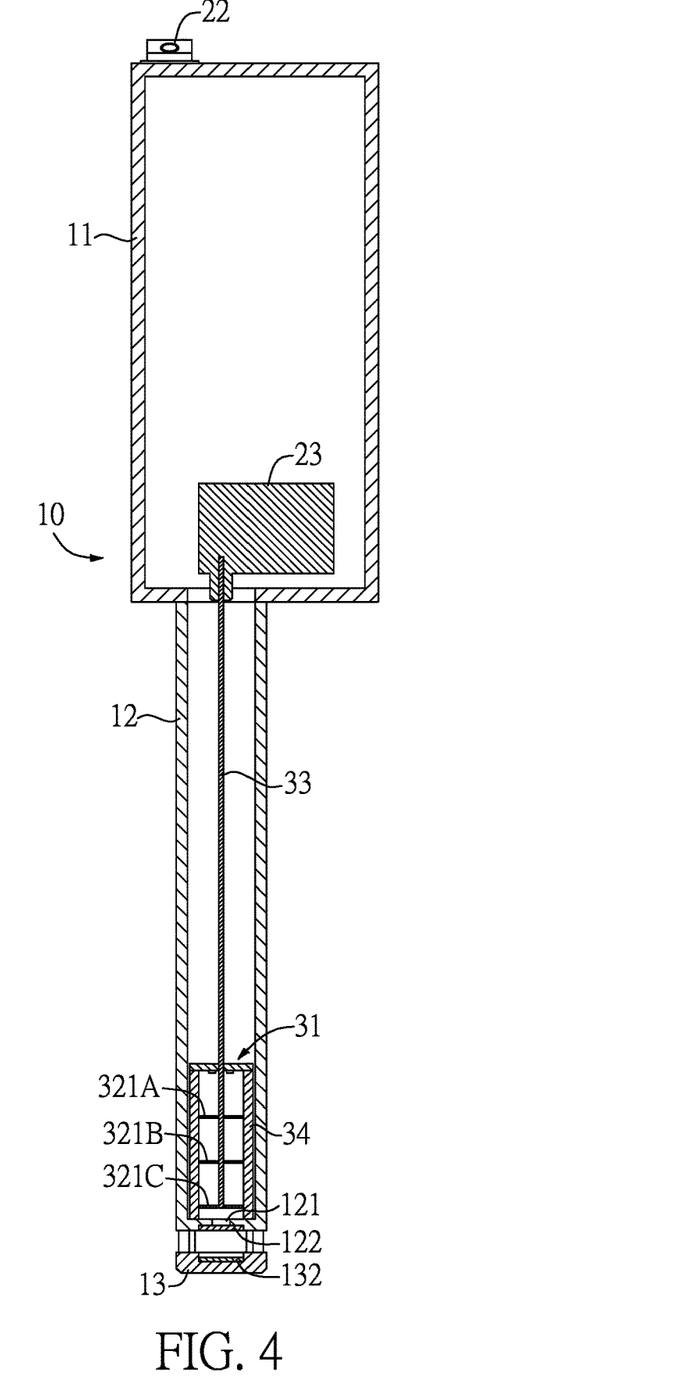
FIG. 4 is a cross-sectional side view of the handheld hemoglobin detecting device in FIG. 1.

As shown in FIGS. 2 and 4, the housing assembly 10 includes a holding base 11, a tubular housing 12, and a liquid holder 13.

The tubular housing 12 extends from the holding base 11, is elongated, and has a distal end surface, a proximal end attached to the holding base 11, a through hole 121, and a protective cover 122. The through hole 121 is formed through the distal end surface of the tubular housing 12. The protective cover 122 is optically transparent, is mounted in the distal end surface of the tubular housing 12, and covers the through hole 121.

Figure 3:
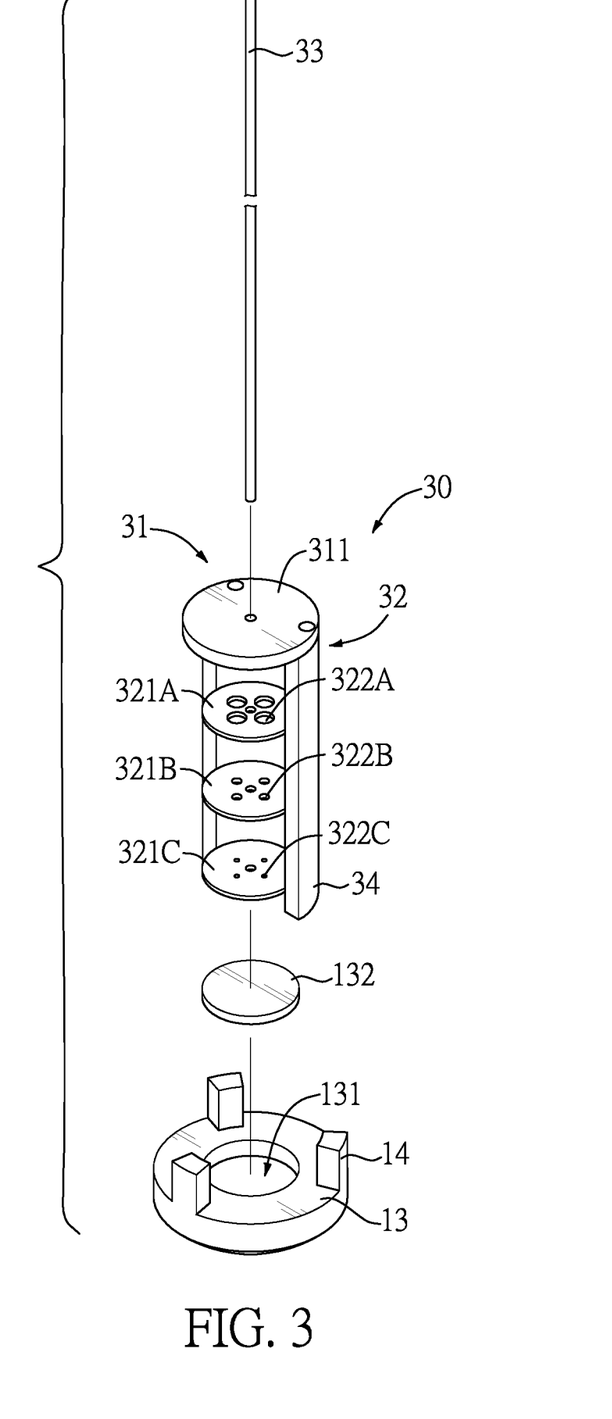
FIG. 3 is an enlarged exploded perspective view of a liquid holder and a lighting assembly of the handheld hemoglobin detecting device in FIG. 1.
Figure 5:
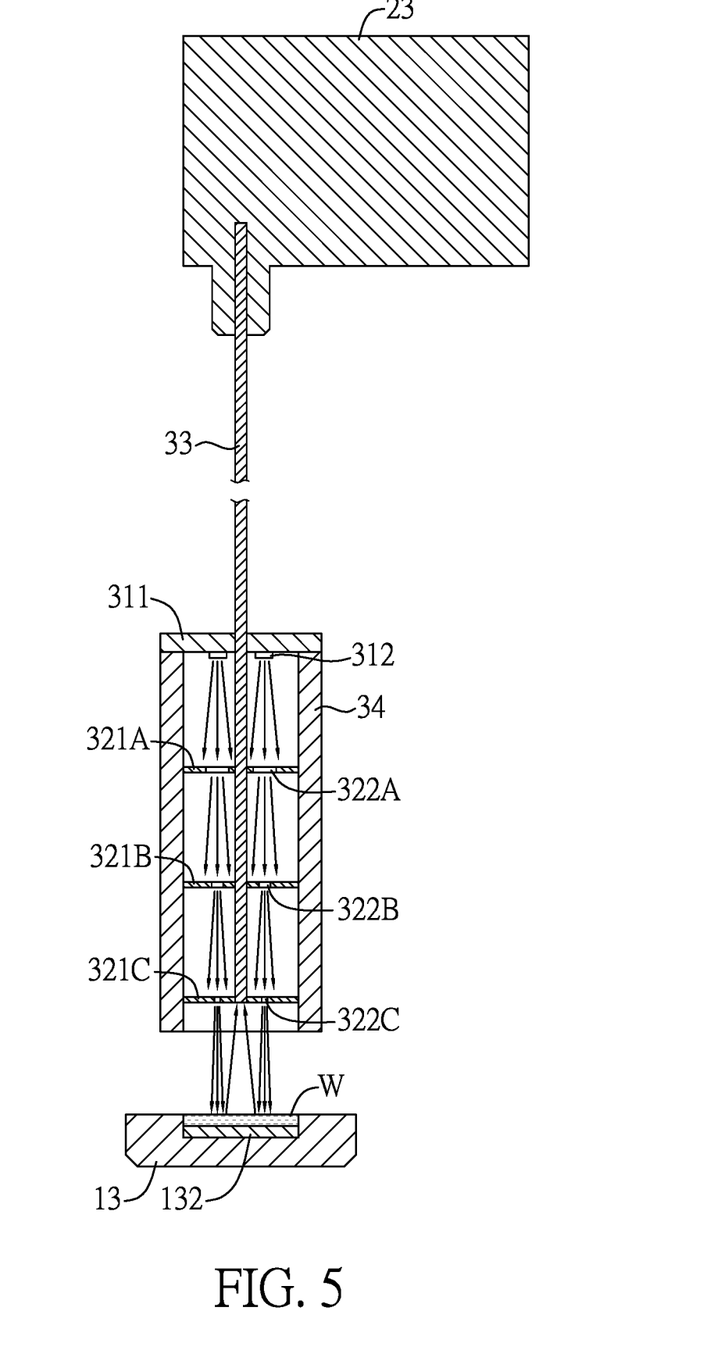
FIG. 5 is an operational enlarged cross-sectional side view of the handheld hemoglobin detecting device in FIG. 1.
Figure 6:
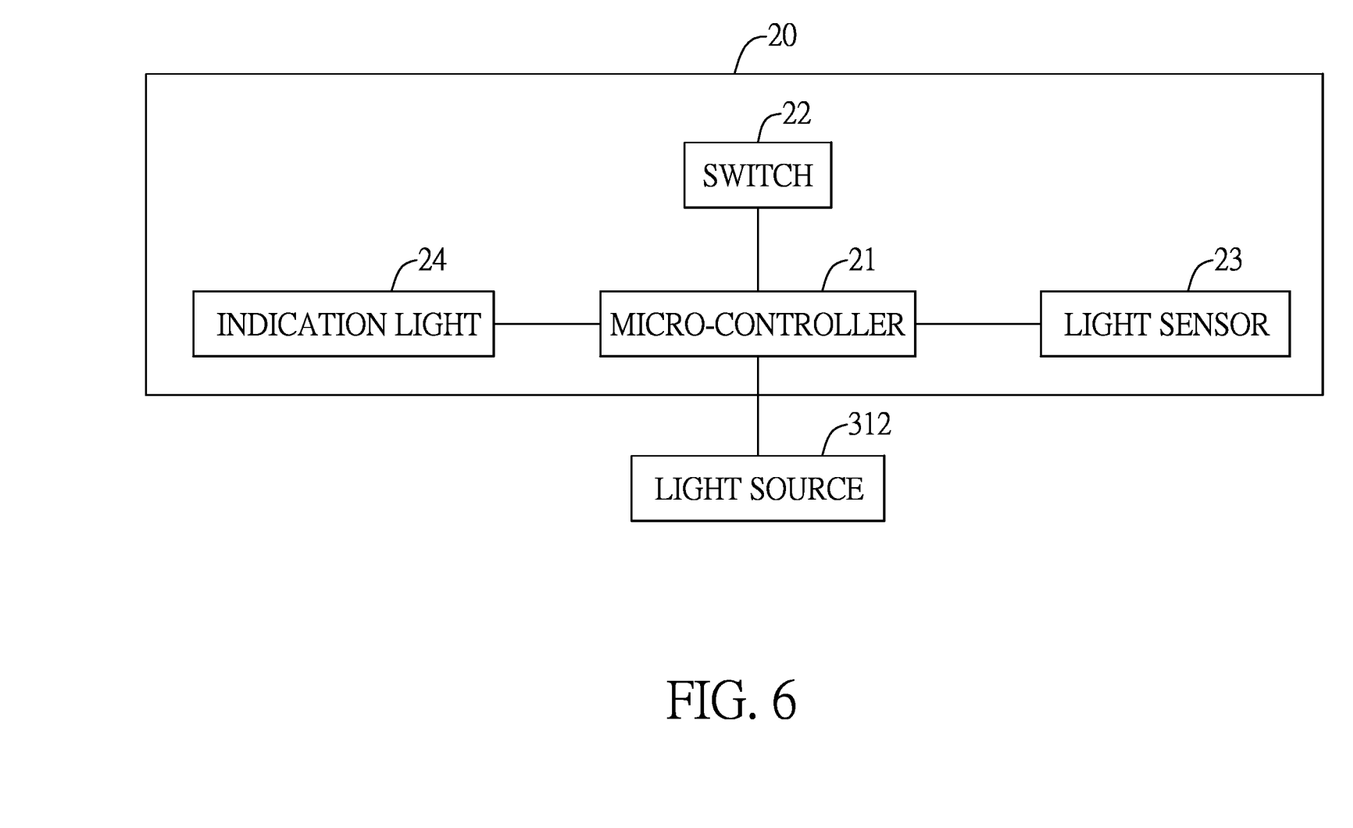
FIG. 6 is a block diagram of the handheld hemoglobin detecting device in FIG. 1.

With further reference to FIGS. 3 and 5, the liquid holder 13 is spaced from the distal end surface of the tubular housing 12 and is attached to the tubular housing 12 via at least one connecting bar 14. The liquid holder 13 has an inner surface, a recess 131, and a light reflector 132. The inner surface of the liquid holder 13 faces toward the distal end surface of the tubular housing 12. The recess 131 is formed in the inner surface of the liquid holder 13. The light reflector 132 is disposed in the recess 131. Specifically, the light reflector 132 is mounted on an inner bottom defined in the recess 131 of the liquid holder 13. Preferably, a distance between the light reflector 132 and the protective cover 122 is less than 20 mm.

With reference to FIGS. 1, 2, 4, and 6, the control module 20 is disposed on the housing assembly 10. Specifically, the control module 20 is disposed on the holding base 11 of the housing assembly 10. The control module 20 includes a micro-controller 21, a switch 22, a light sensor 23, and a display interface 24. The switch 22 is disposed on the holding base 11, is electrically connected to the micro-controller 21 and alternatively switches the micro-controller 21 on or off. The light sensor 23 is mounted in the holding base 11 and is electrically connected to the micro-controller 21. Specifically, the light sensor 23 may be a photodiode array (PDA) detector, a complementary metal-oxide semi-conductor (CMOS) sensor, a charge-coupled device (CCD), or a photo-spectrometer. The display interface 24 is disposed on the holding base 11 and is electrically connected to the micro-controller 21. Specifically, the display interface 24 may include at least one indication light, or may be a display device, such as a screen, a seven-segment display, or the like.

Figure 7:
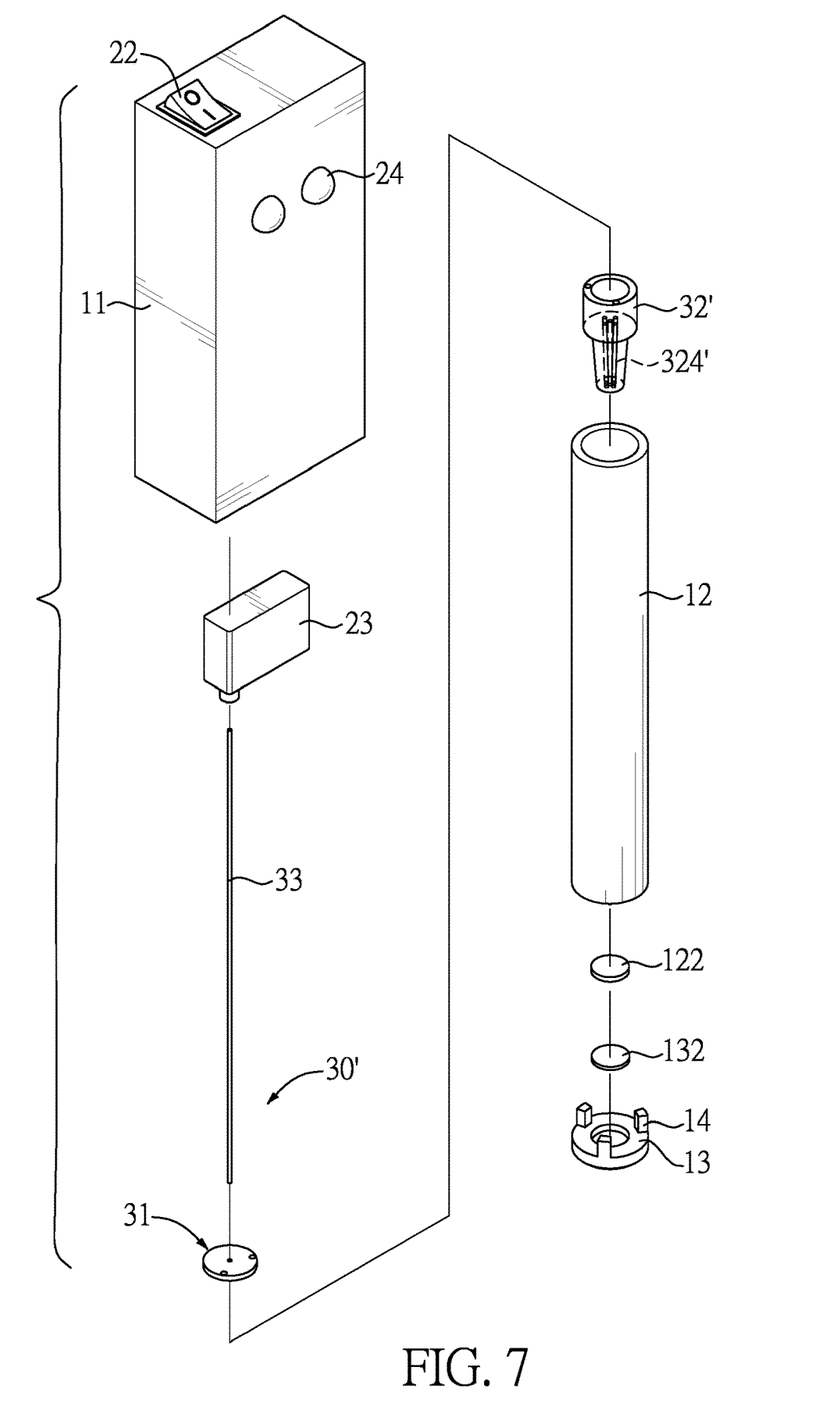
FIG. 7 is an exploded perspective view of a second embodiment of a handheld hemoglobin detecting device in accordance with the present invention.

With reference to FIGS. 2 and 7, the lighting assembly 30, 30' is mounted in the tubular housing 12 and includes a light emitting module 31, a light concentrator 32, 32', and a light guide 33.

The light emitting module 31 is electrically connected to the micro-controller 21 and has a substrate 311 and at least one light source 312. The substrate 311 has a lower surface facing toward the liquid holder 13. The at least one light source 312 is disposed on the lower surface of the substrate 311. Specifically, each of the at least one light source 312 may be a light emitting diode (LED), a laser diode (LD), a high-intensity discharge (HID) lamp, or a halogen lamp.

The light concentrator 32, 32' is disposed between the light emitting module 31 and the liquid holder 13. At least one light beam emitted from the at least one light source 312 passes through and is concentrated by the light concentrator 32, 32' to shine on the liquid holder 13.

With reference to FIGS. 2 to 4, in a first preferred embodiment, the light concentrator 32 comprises multiple partition sheets 321A, 321B, 321C. The partition sheets 321A, 321B, 321C are sequentially arranged separately between the light emitting module 31 and the light holder 13. Each partition sheet 321A, 321B, 321C has at least one aperture 322A, 322B, 322C formed through the partition sheet 321A, 321B, 321C. Each of the at least one aperture 322A, 322B, 322C aligns with one of the at least one aperture 322A, 322B, 322C of each of the other partition sheets 321A, 321B, 321C and aligns with one of the at least one light source 312. Moreover, a diameter of each of the at least one aperture 322A, 322B, 322C of one of the partition sheet 321A, 321B, 321C that is disposed closer to the light emitting module 31 is larger than the diameter of each of the at least one aperture 322A, 322B, 322C of one of the partition sheet 321A, 321B, 321C that is disposed closer to the liquid holder 13 in size. Accordingly, the diameters of the apertures 322A, 322B, 322C decrease from the partition sheet 321A that is disposed closer to the light emitting module 31 to the partition sheet 321C that is disposed closer to the liquid holder 13.

The light guide 33 is formed as an elongated rod and is mounted through the light emitting module 31 and the light concentrator 32. The light guide 33 has an upper end connected to the light sensor 23 and a lower end pointing to the through hole 121 of the tubular housing 12. The light guide 33 transmits light between the lower end and the upper end of the light guide 33. Specifically, the light guide 33 may be an optical fiber and made of glass or plastic, and may has a diameter less than 3.5 mm.

In the first preferred embodiment, the light guide 33 is mounted through the substrate 31 and the partition sheets 321A, 321B, 321C to string up the substrate 31 and the partition sheets 321A, 321B, 321C. The at least one aperture 322A, 322B, 322C of each partition sheet 321A, 321B, 321C includes four apertures 322A, 322B, 322C separately arranged around the light guide 33. Accordingly, the at least one light source 312 of the light emitting module 31 includes four light sources 312. The four light sources 312 generate the light beams that cover most of the visible light frequency bandwidths, which include wavelengths ranging from 350 nm to 650 nm. Specifically, the four light sources 312 may emit a white light, a light with a peak wavelength centered about 380 nm, a light with a peak wavelength centered about 400 nm, and a light with a peak wavelength centered about 420 nm respectively.

In the first preferred embodiment, the multiple partition sheets 321A, 321B, 321C include three partition sheets 321A, 321B, 321C.

In the first preferred embodiment of the present invention, the lighting assembly 30 further includes a mounting bracket 34. The mounting bracket 34 is securely mounted in the tubular housing 12 and has multiple insertion slots 341 sequentially arranged separately between two opposite ends of the mounting bracket 341. The substrate 311 of the light emitting module 31 is securely mounted on the mounted bracket 34. Each partition sheets 321A, 321B, 321C has an engaging protrusion 323A, 323B, 323C radially protruding from a peripheral edge of the partition sheet 321A, 321B, 321C. The engaging protrusions 323A, 323B, 323C of the partition sheets 321A, 321B, 321C are respectively inserted in the insertion slots 341 of the mounting bracket 34. Thus, it is easy to allow each of the at least one aperture 322A, 322B, 322C to align with one of the at least one aperture 322A, 322B, 322C of each of the other partition sheets 321A, 321B, 321C and to align with one of the at least one light source 312, so as to facilitate assembling of the lighting assembly 30.

Figure 8:
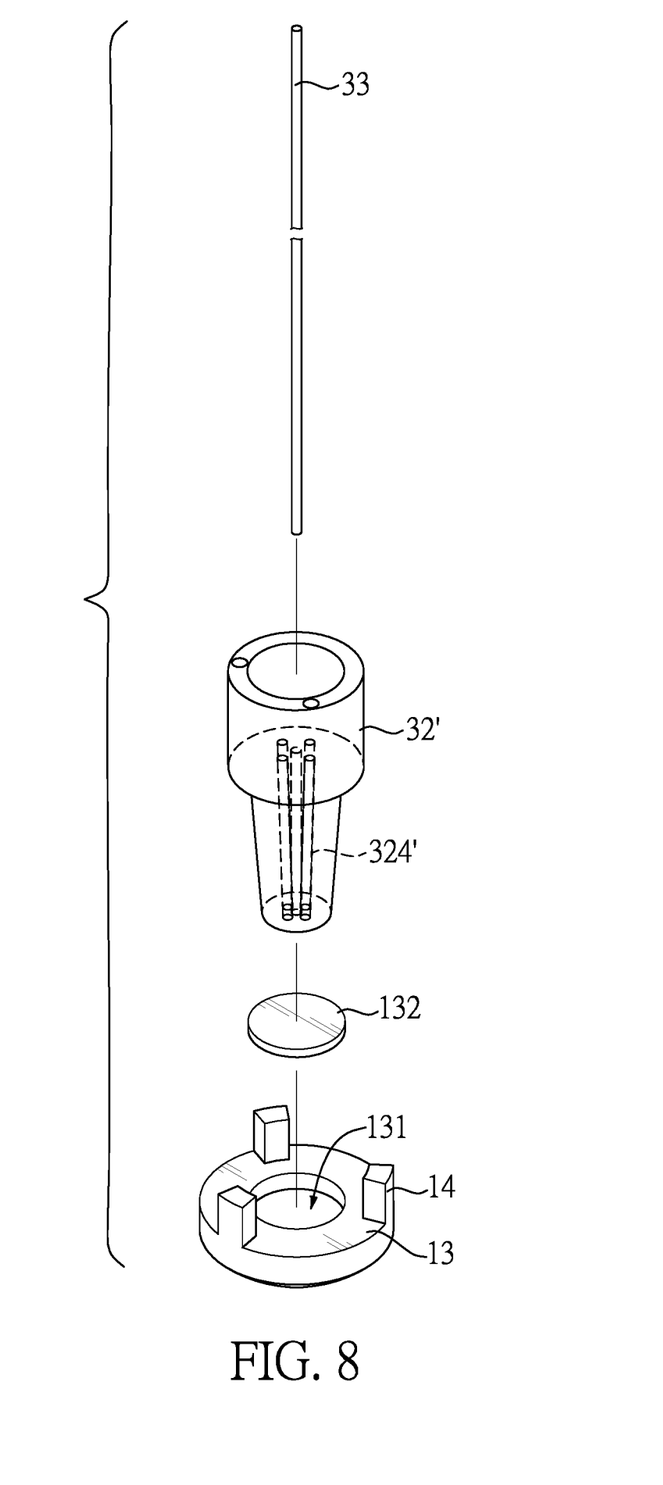
FIG. 8 is an enlarged exploded perspective view of a liquid holder and a lighting assembly of the handheld hemoglobin detecting device in FIG. 7.
Figure 9:
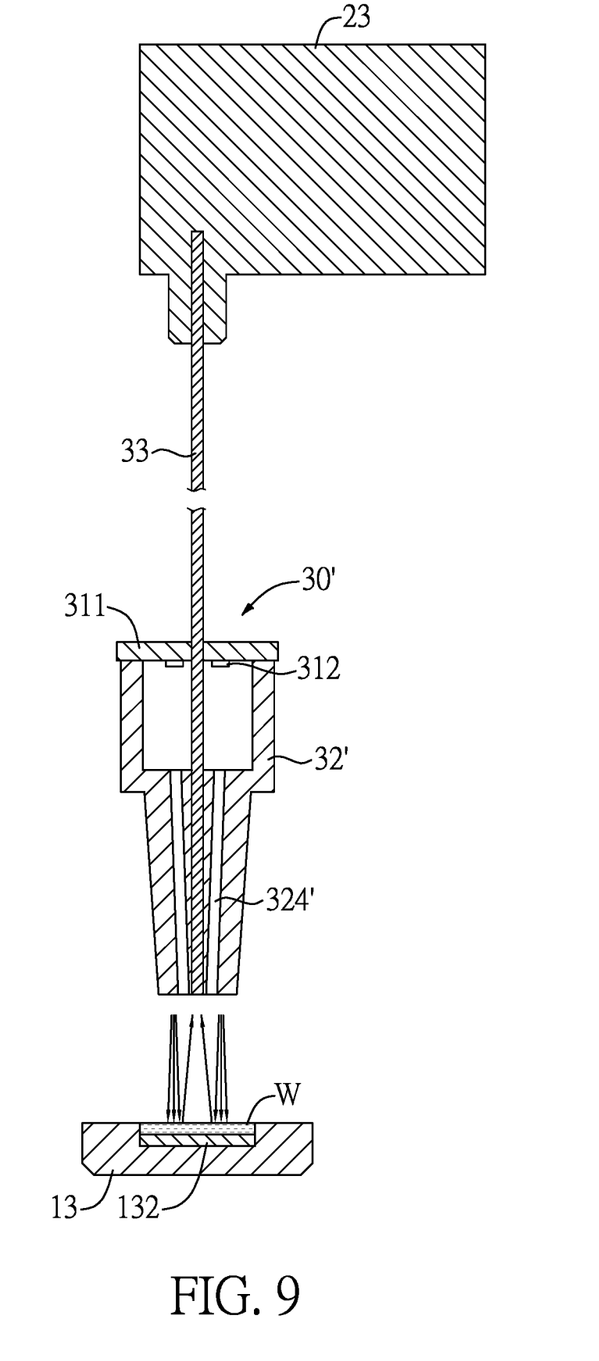
FIG. 9 is a cross-sectional side view of the handheld hemoglobin detecting device in FIG. 7.

With reference to FIGS. 7 to 9, in a second preferred embodiment, the light concentrator 32' has an upper end facing toward the light emitting module 31, a lower end facing toward the liquid holder 13, and at least one light channel 324' formed through the light concentrator 32'. Each of the at least one light channel 324' extends from the upper end of the light concentrator 32' toward a center of the lower end of the light concentrator 32' obliquely. Each of the at least one light source 312 corresponds in position to one of the at least one light channel 324'. Thus, the at least one light beam emitted from the at least one light source 312 passes through the at least one light channel 324' and is centralized to shine on the liquid holder 13. Specifically, the light concentrator 32' may be substantially cone-shaped and tapers from the upper end of the light concentrator 32' to the lower end of the light concentrator 32'.

In the second preferred embodiment, the at least one light channel 324' includes four light channels 324' separately arranged around the light guide 33 and arranged in a conical form. Accordingly, the at least one light source 312 of the light emitting module 31 includes four light sources 312 corresponding in position to the light channels 324' respectively.

Figure 1:
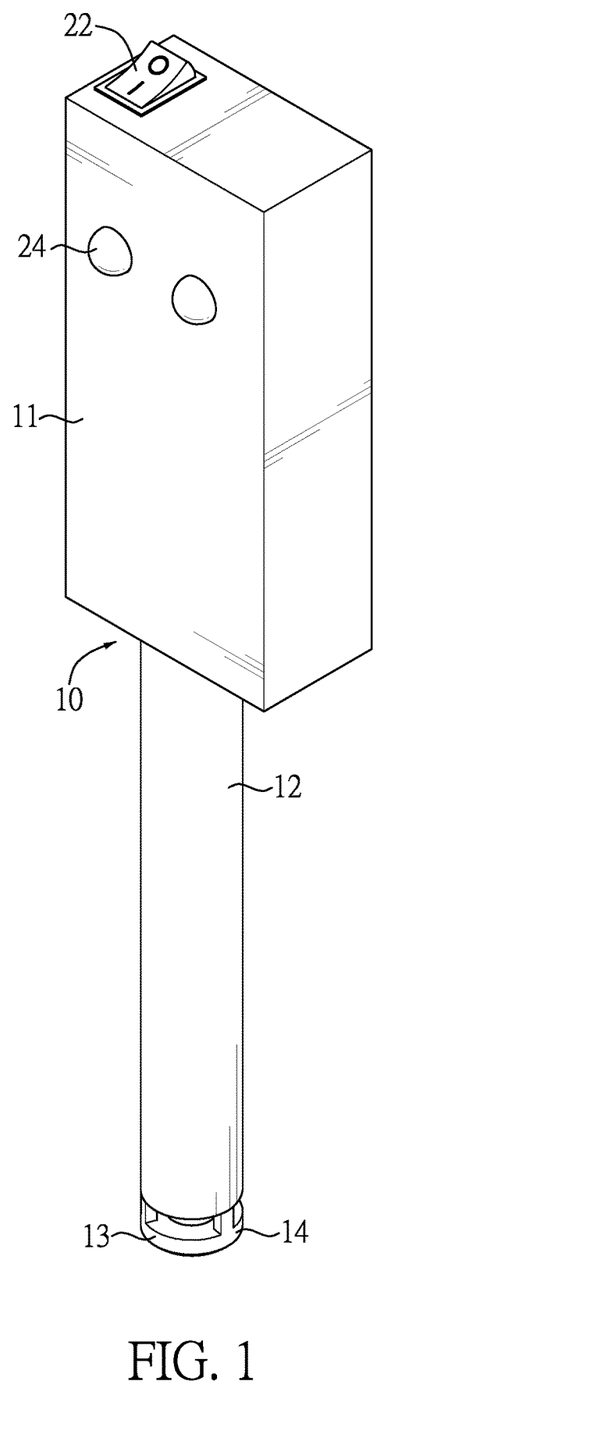
FIG. 1 is a perspective view of a first embodiment of a handheld hemoglobin detecting device in accordance with the present invention.

With reference to FIGS. 1 and 5, when a user intends to detect if there is hemoglobin in excreta water solution W, the user can hold the holding base 11, put the liquid holder 13 into the excreta water solution W to scoop the excreta water solution W with the liquid holder 13. The excreta water solution W is a liquid that includes human fecal extraction, for instance, the liquid solution in a toilet bowl that contains stool. When stool carrying blood tissue falls into the water in the toilet bowl, the blood in the stool will dissolve into the water around it.

Then the user presses the switch 22 to allow each of the at least one light source 312 to emit the light beam. As shown in FIG. 5, in the first preferred embodiment, the light beam passes through the apertures 322 A, 322A, 322C of the partition sheets 321A, 321B, 321C. As shown in FIG. 9, in the second preferred embodiment, the light beam passes through the light channels 324' of the light concentrator 32'. Then the light beam enters the excreta water solution W in the liquid holder 13, and is specularly reflected by the light reflector 132 that is disposed in the recess 131. The light beam that is reflected by the light reflector 132 enters the light guide 33 and is transmitted to the light sensor 23.

The light sensor 23 receives the light beam and generates a light intensity information and sends the light intensity information to the micro-controller 21. The micro-controller 21 determines whether an absorption spectrum of the excreta water solution W matches a target spectrum. Since an absorption spectrum of a blood solution includes peak spectrums about 415 nm, 541 nm, 577 nm, if the absorption spectrum of the excreta water solution W includes peak spectrums about 415 nm, 541 nm, 577 nm, the micro-controller 21 can determine that the absorption spectrum of the excreta water solution W matches the target spectrum. When the absorption spectrum of the excreta water solution W matches the target spectrum, the micro-controller 21 generates a positive result information; when the absorption spectrum of the excreta water solution W does not match the target spectrum, the micro-controller 21 generates a negative result information. The at least one indication light 24 is lighted up accordingly to the positive result information and the negative result information, so as to show the results to the user.

As shown in FIG. 5, the light beam emitted from the at least one light source 312 passes through the apertures 322A, 322B, 322C that align with each other. A diverged portion of the light beam is sequentially blocked by the partition sheets 321A, 321B, 321C with the diameters of the apertures 322A, 322B, 322C decreasing from the partition sheet 321A that is disposed closer to the light emitting module 31 to the partition sheet 321C that is disposed closer to the liquid holder 13. Accordingly, the light beam emitted from the at least one light source 312 is gradually restrained. Only the light beam that is restrained by the apertures 322A, 322B, 322C can enter the light guide 33 after being reflected by the light reflector 132. Day light or light from the environment cannot enter the light guide 33 after being reflected by the light reflector 132. Moreover, as the distance between the light reflector 132 and the protective cover 122 is less than 20 mm, the day light and light from the environment are hard to enter the liquid holder 13. Accordingly, optical noise is reduced and an accuracy in detecting hemoglobin in excreta water solution W is increased.

The handheld hemoglobin detecting device as described has a simplified structure and is easy to assemble. Thus, the handheld hemoglobin detecting device is light and has low manufacturing cost. Moreover, since the partition sheets 321A, 321B, 321C only block the diverged portion of the light beam emitted from the at least one light source 312 and does not influence an emitting direction of the light beam, a lower accuracy in assembling the lighting assembly 30 can be tolerated.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A handheld hemoglobin detecting device comprising:
   a housing assembly including
      a holding base;
      a tubular housing extending from the holding base and having a through hole formed through a distal end surface of the tubular housing; and
      a liquid holder spaced from the distal end surface of the tubular housing, attached to the tubular housing via at least one connecting bar, and having a light reflector disposed in the liquid holder;

a control module disposed on the housing assembly and including
- a micro-controller;
- a switch electrically connected to the micro-controller and alternatively switching the micro-controller on or off;
- a light sensor electrically connected to the micro-controller; and
- a display interface electrically connected to the micro-controller; and a lighting assembly mounted in the tubular housing and including
- a light emitting module electrically connected to the micro-controller and having at least one light source;
- a light concentrator disposed between the light emitting module and the liquid holder, wherein at least one light beam emitted from the at least one light source passes through and is concentrated by the light concentrator to shine on the liquid holder; and
- a light guide mounted through the light emitting module and the light concentrator.

2. The handheld hemoglobin detecting device as claimed in claim 1, wherein the tubular housing of the housing assembly further has a protective cover covering the through hole.

3. The handheld hemoglobin detecting device as claimed in claim 1, wherein
the liquid holder of the housing assembly further has
   an inner surface facing toward the distal end surface of the tubular housing;
   a recess formed in the inner surface of the liquid holder; and
the light reflector is disposed in the recess.

4. The handheld hemoglobin detecting device as claimed in claim 2, wherein
the light concentrator comprises multiple partition sheets sequentially arranged separately between the light emitting module and the light holder, each partition sheet has at least one aperture formed through the partition sheet, and each of the at least one aperture aligns with one of the at least one aperture of each of the other partition sheets and aligns with one of the at least one light source, wherein the light guide is mounted through the partition sheets; and
a diameter of each of the at least one aperture of one of the partition sheet that is disposed closer to the light emitting module is larger than the diameter of each of the at least one aperture of one of the partition sheet that is disposed closer to the liquid holder in size.

5. The handheld hemoglobin detecting device as claimed in claim 4, wherein
the lighting assembly further includes a mounting bracket securely mounted in the tubular housing and having multiple insertion slots, and the insertion slots are sequentially arranged separately between two opposite ends of the mounting bracket;
the light emitting module is securely mounted on the mounted bracket; and
each partition sheets has an engaging protrusion radially protruding from a peripheral edge of the partition sheet, and the engaging protrusions of the partition sheets are respectively inserted in the insertion slots of the mounting bracket.

6. The handheld hemoglobin detecting device as claimed in claim 4, wherein the at least one aperture of each partition sheet includes four apertures separately arranged around the light guide; and the at least one light source of the light emitting module includes four light sources.

7. The handheld hemoglobin detecting device as claimed in claim 5, wherein
the at least one aperture of each partition sheet includes four apertures separately arranged around the light guide; and
the at least one light source of the light emitting module includes four light sources.

8. The handheld hemoglobin detecting device as claimed in claim 6, wherein the four light sources emit a white light, a light with a peak wavelength centered about 380 nm, a light with a peak wavelength centered about 400 nm, and a light with a peak wavelength centered about 420 nm respectively.

9. The handheld hemoglobin detecting device as claimed in claim 6, wherein the four light sources emit a white light, a light with a peak wavelength centered about 380 nm, a light with a peak wavelength centered about 400 nm, and a light with a peak wavelength centered about 420 nm respectively.

10. The handheld hemoglobin detecting device as claimed in claim 4, wherein the multiple partition sheets include three partition sheets.

11. The handheld hemoglobin detecting device as claimed in claim 5, wherein the multiple partition sheets include three partition sheets.

12. The handheld hemoglobin detecting device as claimed in claim 4, wherein a distance between the light reflector and the protective cover is less than 20 mm.

13. The handheld hemoglobin detecting device as claimed in claim 5, wherein a distance between the light reflector and the protective cover is less than 20 mm.

14. The handheld hemoglobin detecting device as claimed in claim 2, wherein
the light concentrator has at least one light channel formed through the light concentrator, each of the at least one light channel extends from an upper end of the light concentrator toward a center of a lower end of the light concentrator obliquely, and each of the at least one light source corresponds in position to one of the at least one light channel; and
the at least one light beam emitted from the at least one light source passes through the at least one light channel and is centralized to shine on the liquid holder.

15. The handheld hemoglobin detecting device as claimed in claim 14, wherein
the at least one light channel includes four light channels separately arranged around the light guide and arranged in a conical form; and
the at least one light source of the light emitting module includes four light sources corresponding in position to the light channels respectively.

16. The handheld hemoglobin detecting device as claimed in claim 15, wherein the four light sources emit a white light, a light with a peak wavelength centered about 380 nm, a light with a peak wavelength centered about 400 nm, and a light with a peak wavelength centered about 420 nm respectively.

17. The handheld hemoglobin detecting device as claimed in claim 14, wherein a distance between the light reflector and the protective cover is less than 20 mm.

18. The handheld hemoglobin detecting device as claimed in claim 2, wherein the display interface includes at least one indication light.

19. The handheld hemoglobin detecting device as claimed in claim 4, wherein the display interface includes at least one indication light.

20. The handheld hemoglobin detecting device as claimed in claim 14, wherein the display interface includes at least one indication light.

* * * * *